US00PP33552P2

(12) United States Plant Patent
Smith

(10) Patent No.: US PP33,552 P2
(45) Date of Patent: Oct. 12, 2021

(54) ***CHRYSANTHEMUM* PLANT NAMED 'CIFZ0078'**

(50) Latin Name: ***Chrysanthemum* x *morifolium***
Varietal Denomination: CIFZ0078

(71) Applicant: SYNGENTA CROP PROTECTION AG, Basel (CH)

(72) Inventor: Mark A. Smith, Alva, FL (US)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 16/892,351

(22) Filed: Jun. 4, 2020

(51) Int. Cl.
*A01H 5/02* (2018.01)
*A01H 6/14* (2018.01)

(52) U.S. Cl.
USPC ..... Plt./289

(58) Field of Classification Search
USPC ..... Plt./289
CPC ... A01H 5/02; A01H 5/00; A01H 6/14; A01H 6/1424
See application file for complete search history.

(56) References Cited

U.S. PATENT DOCUMENTS

PP23,767 P2 * 7/2013 Pieters ..... A01H 6/1424 Plt./289

* cited by examiner

*Primary Examiner* — June Hwu
(74) *Attorney, Agent, or Firm* — Dale Skalla

(57) ABSTRACT

A new garden type *Chrysanthemum* plant named 'CIFZ0078' particularly distinguished by its medium size plant with round mound plant habit, a small size decorative flower (1.5 inch), yellow flower color and a natural season response early October.

1 Drawing Sheet

Latin name of the genus and species of the plant claimed: *Chrysanthemum* x *morifolium*.

Varietal denomination: 'CIFZ0078'.

BACKGROUND OF THE NEW PLANT

The present invention comprises a new *Chrysanthemum*, botanically known as *Chrysanthemum* x *morifolium*, and hereinafter referred to by the variety name 'CIFZ0078'.

'CIFZ0078' is a product of a planned breeding program. The new cultivar has a medium size plant with round mound plant habit, a small size decorative flower (1.5 inch), yellow flower color and a natural season response of early October.

'CIFZ0078' originated from a mutation of X-ray treated cuttings in October 2016 in Gilroy, Calif. 'CIFZ0078' was selected from the resulting plants on Apr. 7, 2017 in Gilroy, Calif.

The female parent was the variety 'CIFZ0046', U.S. Plant Pat. No. 29,108.

TABLE 1

Characteristics of the female parent compared to 'CIFZ0078':

| Trait | 'CIFZ0078' | 'CIFZ0046' |
|---|---|---|
| Natural response: | Couple of days faster | Couple of days slower |
| Blackcloth response: | Similar | Similar |
| Flower color: | Yellow without a two-tone | Orange with darker center creating a two-tone |
| Flower type: | Similar | Similar |
| Plant size: | Similar | Similar |
| Plant habit: | Similar | Similar |

As the new variety is the result of mutation breeding, there is not a male parent.

The first act of asexual reproduction of 'CIFZ0078' was accomplished when vegetative stem cuttings were propagated from the initial selection in January 2016 in Mebane, N.C.

BRIEF SUMMARY OF INVENTION

Horticultural examination of plants grown from cuttings of the plant initiated in January 2016 and continuing thereafter, has demonstrated that the combination of characteristics as herein disclosed for 'CIFZ0078' are firmly fixed and are retained through successive generations of asexual reproduction.

'CIFZ0078' has not been observed under all possible environmental conditions. The phenotype may vary significantly with variations in environment such as temperature, light intensity and day length.

A Plant Breeder's Right for this cultivar was has not yet been applied for. 'CIFZ0078' has not been made publicly available prior to the effective filing date of this application, notwithstanding any disclosure that may have been made less than one year prior to the effective filing date of this application by the inventor or another who obtained 'CIFZ0078' directly from the inventor.

The following traits have been repeatedly observed and are determined to be basic characteristics of the new variety. The combination of these characteristics distinguishes this *Chrysanthemum* as a new and distinct variety.

BRIEF DESCRIPTION OF THE PHOTOGRAPHS

The accompanying photographic drawing shows typical flower and foliage characteristics of 'CIFZ0078' with colors being as true as possible with an illustration of this type.

Figure 1:
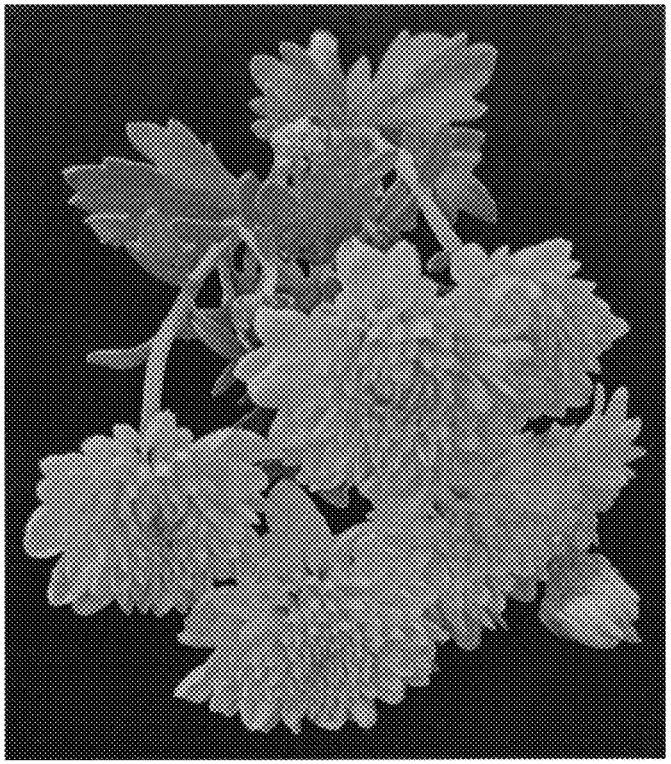
Figure 2:
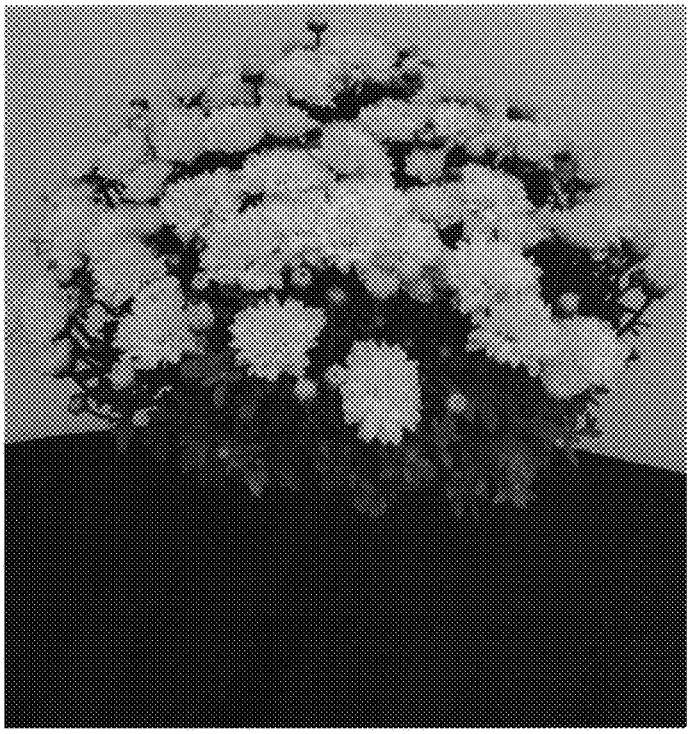

The photographic drawing shows in FIG. 1 a close view of flower of the new variety and in FIG. 2 a flowering plant from an outdoor trial.

The aforementioned photographs, FIG. 1, as well as FIG., 2 were taken in September 2019 both showing a plant from the same black cloth indoor trial in Gilroy, Calif. These plants were about 10 weeks of age. One rooted cutting per pot had been planted in a one gallon pot, not pinched in week 24, and black clothed from week 25. Plants started flowering the end of August.

DETAILED BOTANICAL DESCRIPTION

The measurements were taken in Gilroy, Calif., in September 2019, on the plants from the aforementioned trial.

Color references are made to The Royal Horticultural Society Colour Chart (R.H.S.) 2015.

DIFFERENCES BETWEEN THE NEW VARIETY 'CIFZ0078' AND TWO MOST SIMILAR VARIETIES

TABLE 2

| Trait | 'CIFZ0078' | 'Synwil Yel', U.S. Plant Pat. No. 22,660 |
|---|---|---|
| Natural response: | Couple of days slower | Couple of days faster |
| Black cloth response: | Couple of days slower | Couple of days faster |
| Flower size: | Smaller | Larger |
| Flower color: | Bit darker yellow | Bit lighter yellow |
| Flower type: | Similar | Similar |
| Plant habit: | More even height to width | More width than height |
| Flowering uniformity: | More uniform | Less uniform |

TABLE 3

| Trait | 'CIFZ0078' | 'Espero Yellow', U.S. Plant Pat. No. 23,767 |
|---|---|---|
| Natural response: | Similar | Similar |
| Black cloth response: | Couple days faster | Couple days slower |
| Ray floret length: | 1.5 inch | About 2.5-4.0 cm |
| Flower color: | Bit darker yellow | Bit lighter yellow |
| Flower type: | Similar | Similar |
| Plant size: | Smaller | Larger |
| Plant width: | 36-38 cm | About 60 cm |
| Plant habit: | Similar | Similar |

Plant:

*Form, growth and habit.*—Herbaceous garden-type, stems Upright and outwardly spreading, freely branching, strong and moderately vigorous growth habit.

*Plant height (above soil).*—15-17 cm.

*Plant height (inflorescence included).*—18-22 cm.

*Plant width.*—36-38 cm.

Roots:

*Number of days to initiate roots.*—About 4 days at about 22° C.

*Number of days to produce a rooted cutting.*—14-16 days at 22° C.

*Type.*—Fine, fibrous, free branching.

*Color.*—RHS N155B.

Foliage:

*Arrangement.*—Alternate.

*Immature leaf, color upper surface.*—RHS 137A.

*Immature leaf, color lower surface.*—RHS 137B.

*Mature leaf, color, upper surface.*—RHS 137A.

*Mature leaf, color lower surface.*—RHS 137C.

*Length.*—5.5 cm.

*Width.*—4.8 cm.

*Shape.*—Ovate, with distinct lobes.

*Base shape.*—Attenuate.

*Apex shape.*—Mucronate.

*Margin.*—5-lobed (palmate), edge dentate.

*Number of margin indentations.*—Many.

*Depth of margin indentations.*—Shallow to medium depth.

*Leaf length terminal lobe relative to total leaf length.*—Terminal lobe is ½ to ⅓ the length of the total leaf=Medium.

*Leaf depth lower lateral sinus.*—Shallow.

*Texture, upper surface.*—Bifid hairs.

*Texture, lower surface.*—Bifid hairs.

*Color of veins, upper surface.*—RHS 138B.

*Color of veins, lower surface.*—RHS 138C and transitions to RHS 138B.

*Pattern of veining.*—Palmate.

*Petiole color.*—RHS 138C.

*Petiole length.*—1.5 cm.

*Diameter.*—0.4 cm.

*Texture.*—Bifid hairs.

*Presence of stipules.*—No.

Stem:

*Quantity of main branches per plant.*—5-6.

*Color of stem.*—RHS 138A.

*Length of stem.*—10.0 cm.

*Diameter.*—0.7 cm.

*Length of internodes.*—0.5-1.0 cm.

*Texture.*—Bifid hairs.

*Color of peduncle.*—RHS 138A.

*Length of peduncle.*—5.0 cm.

*Peduncle diameter.*—0.3 cm.

*Texture.*—Bifid hairs.

Receptacle:

*Diameter.*—1.3 cm.

*Height.*—0.8 cm.

*Color.*—RHS 138A.

*Shape.*—Conical.

Inflorescence:

*Type.*—Compositae, solitary, decorative-type inflorescences borne terminally above foliage, ligulate ray florets arranged acropetally on a capitulum giving a double flower.

*Quantity of short days to flowering (response time).*—Approximately 6 weeks.

*Natural season flowering.*—Early October.

*Quantity of inflorescences per plant.*—110-130 with many small buds developing.

*Lastingness of individual blooms on the plant.*—About five weeks from first color.

*Fragrance.*—Slightly spicy.

Bud (when showing color):

*Color.*—RHS 13B.

*Length.*—1.0 cm.

*Width.*—1.2 cm.

*Shape.*—Oblate.

Immature inflorescence (at moment of opening):
*Diameter.*—3.0 cm.
*Color of ray florets, upper surface.*—RHS 13A.
*Color of ray florets, lower surface.*—RHS 13B.
Mature inflorescence:
*Diameter.*—4.0 cm.
*Depth.*—1.0 cm.
*Total diameter of disc.*—No disc present.
*Length of corolla tube.*—Medium.
Ray florets:
*Average quantity of florets.*—150-160 in several whorls.
*Color of florets, upper surface.*—RHS 13B.
*Color lower surface.*—RHS 13A.
*Length.*—1.5 cm.
*Width/diameter.*—0.8 cm.
*Shape.*—Elliptical.
*Apex shape.*—Mostly obtuse and dentate.
*Base shape.*—Tube.
*Ray floret profile in cross section at widest point.*—Petals are moderately concave to start and open to become flat to weakly convex.
*Curvature of the ray floret.*—Petals are straight.
*Margin.*—Entire. Small incisions may be present at tip.
*Margin: type of rolling.*—Weakly involute.
*Texture, upper surface.*—Papillate.
*Lower surface.*—Papillate.
*Ribs present.*—Yes.
*Number of keels.*—1.
Disc florets:
*Number of disc florets.*—0.
Inflorescence (at moment of senescence):
*Color of ray florets, upper surface.*—RHS 12B.
*Color of ray florets, lower surface.*—RHS 12C.
Phyllaries:
*Quantity.*—30-35.
*Color, upper surface.*—RHS 143C.
*Color, lower surface.*—RHS 143A.
*Length.*—0.8 cm.
*Width.*—0.1-0.2 cm.
*Shape.*—Lanceolate.
*Apex shape.*—Acute.
*Base.*—Fused.
*Margins.*—Entire.
*Texture, upper surface.*—Glabrous.
*Texture, lower surface.*—Canescent.
Reproductive organs:
*Pistil.*—One.
*Length.*—0.4 cm.
*Style color.*—RHS 150B.
*Style length.*—0.4 cm.
*Stigma color.*—RHS 7C.
*Stigma shape.*—Bi-parted.
*Ovary color.*—RHS 145C.
*Ovary length.*—0.2 cm.
*Ovary width.*—0.1 cm.
Androecium:
*Stamens.*—These are found on only disc florets only. As no disc florets have been observed there are no specifications possible on the Androecium.
*Fertility/seed set.*—Has not been determined to date.
*Disease/pest resistance.*—Has not been determined to date.
*Hardiness.*—Has not been determined to date.

What is claimed is:

1. A new and distinct variety of *Chrysanthemum* plant named 'CIFZ0078' substantially as illustrated and described herein.

* * * * *